United States Patent
Barancyk et al.

[19]

[11] Patent Number: 6,005,065
[45] Date of Patent: Dec. 21, 1999

[54] AMIDE FUNCTIONAL MONOMERS

[75] Inventors: Steven V. Barancyk; Neil D. McMurdie, both of Pittsburgh; James B. O'Dwyer, Valencia, all of Pa.

[73] Assignee: PPG Industries Ohio, Inc., Cleveland, Ohio

[21] Appl. No.: 09/138,255

[22] Filed: Aug. 21, 1998

Related U.S. Application Data

[62] Division of application No. 08/681,050, Jul. 22, 1996, Pat. No. 5,859,174.

[51] Int. Cl.$^6$ ............ C08G 73/00; C08G 69/00; C07C 229/00
[52] U.S. Cl. ............ 528/310; 528/170; 528/322; 562/455
[58] Field of Search .................. 528/170, 310, 528/322; 562/455

[56] References Cited

U.S. PATENT DOCUMENTS

| | | | |
|---|---|---|---|
| 2,458,420 | 1/1949 | Reynolds et al. | 260/83 |
| 3,366,613 | 1/1968 | Kelley | 260/89.5 |
| 4,147,679 | 4/1979 | Scriven et al. | 260/29.2 TN |
| 4,220,679 | 9/1980 | Backhouse | 427/401 |
| 4,403,003 | 9/1983 | Backhouse | 427/407.1 |
| 4,543,276 | 9/1985 | Parekh | 427/388.3 |
| 4,919,514 | 4/1990 | Ebert et al. | 350/96.34 |
| 5,053,463 | 10/1991 | Inoue | 525/427 |
| 5,071,904 | 12/1991 | Martin et al. | 524/458 |
| 5,098,947 | 3/1992 | Metzger et al. | 524/507 |
| 5,124,433 | 6/1992 | Inoue | 528/272 |
| 5,196,485 | 3/1993 | McMonigal et al. | 525/327.3 |
| 5,300,537 | 4/1994 | Muller et al. | 523/115 |
| 5,374,682 | 12/1994 | Gouda et al. | 525/185 |
| 5,445,850 | 8/1995 | Das et al. | 427/407.1 |
| 5,780,559 | 7/1998 | Humbert et al. | 525/452 |

FOREIGN PATENT DOCUMENTS

| | | |
|---|---|---|
| 0 257 848 | 3/1988 | European Pat. Off. . |
| 0 262 255 | 4/1988 | European Pat. Off. . |
| 0 697 400 | 2/1996 | European Pat. Off. . |
| 697400A2 | 2/1996 | European Pat. Off. . |
| 49-18126 | 2/1974 | Japan . |
| 6-184073 | 7/1994 | Japan . |
| 8-59950 | 3/1996 | Japan . |

OTHER PUBLICATIONS

Patent Abstracts of Japan, vol. 18, No. 639, Dec. 1994 for JP 06–247917 to Nippon Shokubai Co., Ltd.

"Castor–based Derivatives: Synthesis of Some Acrylate Esters", J. Am. Oil Chem. Soc. (1966), Janes Shields, et al., pp. 542–545.

Patent Abstracts of Japan, vol. 15, No. 149, for JP 03–21910 to Sumitomo Electric Ind. Ltd.

*Primary Examiner*—P. Hampton-Hightower
*Attorney, Agent, or Firm*—Kenneth J. Stachel; Krisanne Shideler; Ann Marie Cannoni

[57] ABSTRACT

Ethylenically unsaturated compounds are provided having the structure:

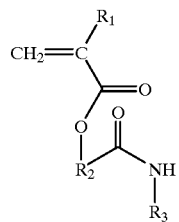

wherein $R_1$ is hydrogen or methyl, $R_2$ is a divalent linking group having 2 to 20 carbon atoms such as alkylene groups, and $R_3$ is hydrogen or lower alkyl having 1 to 4 carbon atoms, and when $R_3$ is hydrogen and $R_2$ has two carbon atoms $R_2$ is methyl methylene.

12 Claims, No Drawings

AMIDE FUNCTIONAL MONOMERS

This is a divisional of U.S. patent application Ser. No. 08/681,050, filed Jul. 22, 1996, now U.S. Pat. No. 5,859,174.

FIELD OF THE INVENTION

The present invention relates to novel ethylenically unsaturated monomers having amide functionality and amide functional polymers including those produced with such monomers.

BACKGROUND OF THE INVENTION

Acrylic polymers curable with aminoplasts like melamine aldehyde condensates are formulated with other components into useful coating compositions for a variety of substrates. Generally, the curing mechanism is through ether linkages formed by the reaction of the melamine aldehyde condensate and the hydroxyl functionality of the acrylic polymer. Coatings based on this type of cure chemistry on some substrates that are exposed to the environment can develop acid etching defects from the more acidic natural phenomenon such as acid rain. Additionally, acrylic and other ethylenically unsaturated monomers like acrylamide, methacrylamide and N-methyl acrylamide are useful in the production of polymers that can be used in coating compositions. The amide functionality allows for crosslinking with aminoplast-type crosslinking agents to provide cured coatings with desirable properties such as mar resistance and solvent resistance.

Japanese Kokai 6-184073 (A) discloses 2-carbamoylethyl methacrylate monomer. Acrylamide and methacrylamide are among other known amide functional monomers. These monomers of the prior art are relatively hydrophilic such that it may be difficult to use them in large amounts in polymers that will be formulated into solvent borne coating compositions.

It would be desirable to provide amide functional monomers that can be copolymerized with ethylenically unsaturated monomers and that yield amide functional polymers and to provide amide functional polymers where such polymers are suitable for use in formulating waterborne and/or solventborne coating compositions capable of producing coatings with increased resistance to acid etching while maintaining other desirable properties.

SUMMARY OF THE INVENTION

In accordance with the present invention, ethylenically unsaturated compounds are provided having the structure:

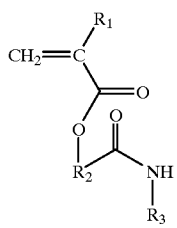

Structure I wherein $R_1$ is hydrogen or methyl, $R_2$ is a divalent linking group having 2 to 20 carbon atoms such as an alkylene group, and $R_3$ is hydrogen or lower alkyl having 1 to 4 carbon atoms; wherein when $R_3$ is hydrogen and $R_2$ has two carbon atoms, $R_2$ is methyl methylene.

Also provided are polymers prepared from the above compounds and/or other amide functional compounds that are copolymerized with other ethylenically unsaturated monomers via addition polymerization. The resulting polymers contain a plurality of groups of the structure:

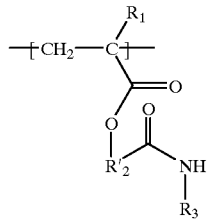

Structure II wherein $R_1$ and $R_3$ are as defined above, and when $R'_2$ contains urethane linkages, the polymers contain less than about 2% by weight acid functionality, based on the total solid weight of monomers used to prepare the polymers. That is, ethylenically unsaturated monomers having acid functionality are used to prepare the polymers in amounts less than about 2% by weight, based on the total solid weight of monomers used to prepare the polymers.

DETAILED DESCRIPTION

For the chemical structures disclosed and claimed herein none of these structures are intended to depict or to be limited to any particular bond angles of the atoms, but the chemical structures depict which atoms are bonded to adjacent atoms in the structure.

The ethylenically unsaturated compounds of the present invention having the structure of Structure I preferably has methyl as $R_1$ and has an alkylene group with 2 to 13 carbon atoms as $R_2$. Generally, $R_2$ may be cycloaliphatic, linear or branched aliphatic such as alkylene including ethylene, methyl ethylene, propylene, dimethyl propylene, butylene, pentylene, hexylene, and the like, and may be inertly substituted such as with alkyl groups. Also $R_2$ may further include functional linkages such as urethane, ester, amide, ether, and the like. Preferably for coatings application, $R_2$ does not include aromatic functionality such as aralkylene. Though not intending to be bound by any theory, it is believed that aromatic functionality causes yellowing of coatings containing polymers with such functionality. Most preferably, $R_2$ is pentylene. Likewise, $R_3$ may be linear or branched aliphatic such as methyl, methyl ethyl, propyl, methyl propyl, butyl, and the like, and may be inertly substituted. $R_3$ may be hydrogen although lower alkyl groups are preferred such that the compound is a secondary amide. Most preferably, $R_3$ is methyl. When $R_3$ is hydrogen and $R_2$ has two carbon atoms, $R_2$ is a branched (methyl methylene) group.

The compounds of the present invention may be prepared by reacting a hydroxyl functional amide with (meth)acrylic acid or anhydride at any temperature and pressure and for a period of time for the reaction to proceed. Preferably, the reaction of the hydroxyl functional amide with an anhydride is performed at a temperature ranging from about 50 to about 100° C. at times ranging from about 8 to about 48 hours. A catalyst may optionally be employed, which can be a basic catalyst such as sodium hydroxide, sodium carbonate, sodium hydrogen carbonate, tertiary amines such as triethylamine, 2,2,2-diazabicyclooctane, N,N,-dimethylaniline, pyridine, dialkyl amino pyridines, polydimethylaminopyridine, 4-dimethylaminopyridine, 4-methylorpholine, N-methylpiperazine, N-methylpiperidine, and organic bases such as quaternary ammonium hydroxides, 4-pyrrolidinopyridine, and imidazole. The amount of catalyst is not critical and may, for example, be as low as about 6 p.p.m. When a catalyst is used, 4-dimethylaminopyridine is preferred.

An inhibitor may also be included to prevent premature polymerization of the product monomer, where the polymerization inhibitor can be any conventional polymerization inhibitor known to those skilled in the art. Without limitation the inhibitor may be chosen from the following classical inhibitors, for example from sterically hindered phenols such as 4-tert-butylpyrocatechol, 2,6-di-tert-butyl-4-methylphenol, which is preferred, N-nitrosodi-phenylamine, p-tert-butylcatechol, phenothiazine, N-phenyl-naphthylamine, 2,2'-methylene-bis-(4,6-di-tert-butylphenol), 2,2'-methylenebis(6-tert-butyl-4-methylphenol) available as 2,2,4,6-Ralox® and Ralox® 46 antioxidants from Raschig GmbH, Germany, p-methoxyphenol and di-tert-butyl-p-cresol. The inhibitor can be employed in a proportion of between approximately 0.1% and up to 1.0% by weight relative to the monomer(s) depending on the specific inhibitor used.

The compounds may also be prepared by transesterification of (meth)acrylic acid esters with a hydroxyl functional amide. The transesterification reaction can be performed at conditions of temperature, time, and pressure as known to those skilled in the art for transesterification reactions. Preferably, the transesterification is conducted at temperatures ranging between about 90 to about 115° C. and at times between about 6 to about 16 hours in the presence of a transesterification catalyst such as dibutyltin oxide or lithium hydroxide. Although other conventional transesterification catalysts known to those skilled in the art can be used such as: titanium alkoxides, like titanium (IV) butoxide, titanium (IV) propoxide, and titanium tetraisopropoxide; manganese acetate; zinc acetate; alkyl titanate, like isopropyl titanate, n-butyl titanate; alkyl zirconate, like n-propyl zirconate; dialkyl tin acetate halide, like dibutyl tin acetate chloride; and dialkyl tin dialkyl ester, like dibutyl tin diacetate and dibutyl tin dilaurate, and tin octoate. These catalysts can be used in approximate amounts of 0.1 to 2% by weight of the monomer reactants. Preferably, a three to five fold molar excess of the (meth)acrylate ester is employed. The by-product alcohol can be removed by distillation; in the case of ethyl acrylate, it is removed as an ethanol/ethyl acrylate azeotrope. Inclusion of an inhibitor, as discussed above, and sparging the reaction mixture with air are preferably used to prevent polymerization of the reaction mixture. In this reaction the preferred inhibitor is 4-methoxyphenol.

Suitable hydroxyl functional amides have the following structure:

Structure III

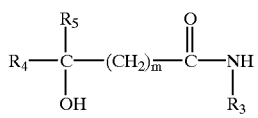

where $R_3$, $R_4$ and $R_5$ are each independently hydrogen or alkyl having 1 to 4 carbon atoms and m is an integer from 0 to 6. When m=0 either $R_4$ or $R_5$ is alkyl. $R_3$ preferably is the same group as $R_3$ in Structures I and II. Such hydroxyl functional amides may be prepared by reacting a hydroxyl functional acid or ester with ammonia or a primary amine by any method known to those skilled in the art. Examples of hydroxyl functional acids and esters include lactic acid and ethyl lactate, respectively, including mixtures thereof and other hydroxyfunctional monocarboxylic acid and esters known to those skilled in the art. The reaction with the lower alkyl esters like lactates may be conveniently carried out at ambient pressure either neat or in aqueous or alcoholic media at temperatures ranging from about 0 to about 50° C. at times ranging from about 2 to about 120 hours. Aqueous ammonium hydroxide or commercially available aqueous solutions of the lower alkyl amines can be used. Preferably, "lower alkyl" means the hydrocarbon group has 1 to 4 carbon atoms. Solvent and by-product alcohol can be conveniently removed from the product under reduced pressure and maximum temperatures of about 60° C. In instances in which water is present in the reaction, residual water not removed during the reduced pressure strip can be removed from the hydroxyl functional amide by azeotropic reflux at ambient pressure with a solvent such as cyclohexane or toluene or other similar solvents known to those skilled in the art.

Alternatively, the hydroxyl functional amides may be prepared by ring-opening a lactone with ammonia or a primary amine. Examples of suitable lactones include those of the following general formula:

Structure IV

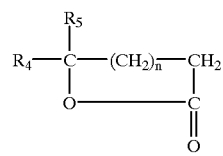

where $R_4$ and $R_5$ are as defined above, and n is an integer from 1 to 3. Suitable lactones include caprolactones such as gamma-caprolactone, delta-caprolactone, epsilon-caprolactone, monoalkyl caprolactones, such as methyl- and ethyl-epsilon-caprolactone, butyrolactone, dialkyl caprolactones, such as dimethyl- and diethyl-epsilon-caprolactone, and the like. Preferably, the lactone is epsilon-caprolactone.

Suitable primary amines include lower alkyl amines such as methylamine, ethylamine, propylamine, butylamine, and the like. Preferably, the lactone is ring-opened with ammonia or methylamine. The reactions are preferably conducted in aqueous media and at ambient pressure, although pressures above atmospheric pressure can be used, at times in the range from about 4 to about 36 hours and at temperatures ranging from about 0 to about 50° C. The aqueous media can employ ammonia or methylamine in aqueous solution of course, the foregoing conditions vary within the specified ranges depending on the particular reactants used. Upon completion of the reaction, water is preferably removed from the product under reduced pressure. A minimum pressure of 1 to 2 mm and maximum temperature of around 60° C. are preferred. Any residual water that may not be removed during the reduced pressure strip can be removed from the hydroxyl functional amide by azeotropic reflux at ambient pressure with a solvent such as cyclohexane or toluene.

The compounds of the present invention are ethylenically unsaturated and may be reacted via addition polymerization with other ethylenically unsaturated monomers to form polymers. The resulting polymers contain a plurality of groups of Structure II above. The polymer is preferably a copolymer, and the copolymer may be a random copolymer of 2 or more different monomers which can include the compounds of the present invention and/or the aforediscussed reaction product resulting in R'$_2$ as Structure V. Also, the copolymer may be a blocked or segmented (segmented means a short block that occurs more frequently than the longer block) copolymer of two or more different monomers. The random copolymers are preferred because of their relative ease of synthesis. All possible copolymer repeat unit sequences and tacticity sequences may co-exist in the copolymers of this invention.

In Structure II, $R_1$, R'$_2$, and $R_3$ are as defined above, and $R_3$ is preferably lower alkyl, more preferably methyl or butyl. Though not intending to be bound by any theory, it is believed that when $R_3$ is alkyl, coating compositions containing such polymers exhibit improved durability with respect to color retention during accelerated weather testing.

In one embodiment of the polymer of the present invention, the reaction product of a hydroxyl functional vinyl monomer such as hydroxyethyl methacrylate and the like, a diisocyanate, and a hydroxyl functional amide such as a lactone that has been ring opened with ammonia is one of the compounds to form the polymer. In this embodiment, R'$_2$ of Structure II contains urethane linkages.

Examples of suitable aromatic diisocyanates are 4,4'-diphenylmethane diisocyanate and toluene diisocyanate. Examples of suitable aliphatic diisocyanates are straight chain aliphatic diisocyanates such as 1,6-hexamethylene diisocyanate. Also, cycloaliphatic diisocyanates can be employed. Examples include isophorone diisocyanate, which is preferred, and 4,4'-methylene-bis-(cyclohexyl isocyanate).

One particular such reaction product for forming the polymer is the reaction product of hydroxyethyl methacrylate, isophorone diisocyanate, and 6-hydroxycaproamide, and R'$_2$ of Structure II has the structure:

aforementioned reaction product monomer resulting in Structure V include virtually any known to those skilled in the art such as acid functional monomers including, for example, itaconic acid, acrylic acid, and methacrylic acid. Monomers having acid functionality are typically used in amounts of about 1 to 5% preferably about 1 to 3%. When copolymerized with amide functional compounds of the present invention derived from diisocyanates; i.e., when R'$_2$ contains urethane linkages like that of Structure V, the acid functional monomers are used in amounts of about 2% by weight or less. These weight percentages are based on the total weight of the monomers added together to prepare the polymer. Other suitable ethylenically unsaturated monomers that can be reacted with the compounds of the present invention include acrylamide, methacrylamide, and alkyl esters of acrylic acid or methacrylic acid such as methyl methacrylate, ethyl methacrylate, butyl methacrylate, ethyl acrylate, butyl acrylate, 2-ethylhexyl acrylate, and the like.

Additional suitable polymerizable ethylenically unsaturated monomers include vinyl aromatic compounds such as styrene and vinyl toluene; acrylamide; methacrylamide; nitriles such as acrylonitrile and methacrylonitrile; vinyl and vinylidene halides such as vinyl chloride and vinylidene fluoride and vinyl esters such as vinyl acetate. Hydroxyl functional monomers such as hydroxyethyl acrylate, hydroxypropyl acrylate, hydroxyethyl methacrylate, and hydroxypropyl methacrylate may also be copolymerized with the other acrylic monomers. When the amide functional monomer is one where $R_3$ of Structure II is hydrogen, monomers having hydroxyl functionality are typically used in amounts of about 1 to 10% by weight, preferably less than 10% by weight. Most preferably, when $R_3$ is hydrogen the polymer has a hydroxyl value less than about 100. The ethylenically unsaturated compounds of the present invention are typically used to prepare the polymers in an amount of about 40 to 70%, preferably about 40 to 60%. All Structure V

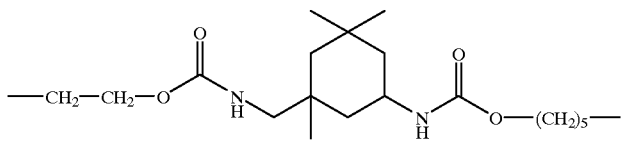

For the polymer of this embodiment, the hydroxyl functional amide is preferably initially reacted with the isocyanate at a maximum temperature of around 60° C. in a suitable solvent. Dibutyltin dilaurate is preferably employed as a catalyst for the reaction, but other catalysts for the reaction of hydroxyl groups with isocyanate groups known in the art may also be used. A ratio of hydroxyl groups on the hydroxyl functional amide monomer to isocyanate groups of about 0.5 to about 0.7 is preferably employed. This minimizes the amount of unreacted isophorone diisocyanate remaining upon completion of the initial step and thus minimizes formation of di(meth)acrylate adduct in the following step. A hydroxyl functional meth(acrylate) monomer is preferably reacted with the remaining isocyanate functional groups at a temperature less than about 100° C., most preferably between 65 and 75° C. An inhibitor, as discussed above, can be included in the reaction to prevent polymerization. Upon completion of the reaction, the monomer can be reduced with a suitable solvent, relatively polar solvents such as alcohols are preferred.

Suitable ethylenically unsaturated monomers that can be reacted with the compounds of the present invention and the percentages given are by weight, based on the total solid weight of monomers used to prepare the polymer.

The acrylic polymer may be prepared by solution polymerization techniques in the presence of suitable initiators such as organic peroxides or azo compounds, for example, benzoyl peroxide or N,N-azobis(isobutyronitrile). The polymerization may be carried out in an organic solvent in which the monomers are soluble by techniques conventional in the art.

Other polymerization techniques include aqueous emulsion or dispersion polymerization techniques that are well known in the art. The polymers of the present invention may be waterborne or solventborne. They are preferably solventborne.

The acrylic polymer having a plurality of groups of Structure II typically has a number average molecular weight of from about 1000 to 10,000, preferably from about 1000 to 5000 as determined by gel permeation chromatography using a polystyrene standard, and a weight average molecular weight of from about 1500 to 20,000, preferably from about 2000 to 6000 as determined by gel permeation chromatography using a polystyrene standard. The polymer typically has a hydroxyl value less than about 100 and an amide equivalent weight less than about 1000, preferably within the range of about 200 to about 600, based on equivalents of reactive amide groups. The equivalent weight is a calculated value based on the relative amounts of the various ingredients used in making the polymer and is based on solids of the polymer.

Polymers prepared from the monomers of the present invention are useful in coating compositions containing aminoplasts or other crosslinking agents which have active hydrogens that are reactive with amide functionality. Such coating compositions are particularly useful in automotive applications because they exhibit superior mar, solvent, and acid etch resistance. The coating compositions may be solventborne or waterborne.

The invention will be further described by reference to the following examples. Unless otherwise indicated, all parts are by weight.

EXAMPLE A

A material containing both hydroxyl and amide functional groups was prepared from the following ingredients:

| Ingredients | Weight in grams |
| --- | --- |
| ε-caprolactone | 3000.0 |
| ammonium hydroxide | 3100.0 |
| lithium hydroxide hydrate solution (58 g in 750 g methanol) | 808.0 |
| ethyl acetate | 2750.0 |
| isopropanol | 250.0 |
| ethyl acetate | 2750.0 |

ε-Caprolactone was charged to a flask equipped with a mechanical stirrer and thermometer and cooled in an ice bath to below 5°C. A pre-cooled 30% solution of ammonium hydroxide was added and the reaction temperature was maintained below 5° C. until all ε-caprolactone was consumed as indicated by gas chromatography. The water and excess ammonia were vacuum stripped at 50° C. at the completion of which the acid value was measured to be 2300. The acid by-product was removed via flocculation by addition of lithium hydroxide hydrate in methanol solution and ethyl acetate followed by isopropanol until clarified. A second portion of ethyl acetate was added and the flocculated acid was filtered. All solvents were stripped under reduced pressure at 50° C. to yield 6-hydroxycaproamide (2750 g) as a pale yellow oil which crystallized upon standing at room temperature. Gas chromatographic and NMR spectral data indicated greater than 95% purity.

EXAMPLE B

An amide methacrylate monomer was prepared from the following ingredients:

| Ingredients | Weight in grams |
| --- | --- |
| 6-hydroxycaproamide of Example A | 249.0 |
| methacrylic anhydride | 328.0 |
| 2,6-di-t-butyl-4-methylphenol | 1.2 |
| triphenyl phosphite | 0.6 |
| toluene | 500.0 |
| sodium hydroxide | 88.0 |
| deionized H$_2$O | 400.0 |
| deionized H$_2$O | 200.0 |
| deionized H$_2$O | 200.0 |

To a flask equipped with a mechanical stirrer, thermocouple, and condenser were added 6-hydroxycaproamide, methacrylic anhydride, 2,6-di-t-butyl-4-methylphenol, and triphenyl phosphite. The contents were heated to 90° C. and held until all 6-hydroxy-caproamide was consumed as indicated by gas chromatography. The contents were cooled to room temperature and toluene was added. A solution of sodium hydroxide in water was added over 20 minutes and stirring was maintained for 30 minutes. The contents were transferred to a separatory funnel and the aqueous phase was removed. The organic phase was washed with two equal portions of deionized water and the toluene was removed under reduced pressure at 80° C. The product (330 g) was a pale yellow liquid which crystallized upon standing at room temperature. Gas chromatography of the product indicated about 95% purity and NMR spectral data were consistent with the 6-carboaminohexyl methacrylate structure.

EXAMPLE C

An acrylic copolymer of the amide methacrylate monomer of the previous example was prepared from the following ingredients:

| Ingredients | Weight in grams |
| --- | --- |
| Charge 1 | |
| DOWANOL PM[1] | 300.0 |
| EXXATE 600[2] | 300.0 |
| Charge 2 | |
| LUPERSOL 555M60[3] | 180.0 |
| DOWANOL PM | 90.0 |
| EXXATE 600 | 90.0 |
| Charge 3 | |
| 6-carboaminohexyl methacrylate of Example B | 900.0 |
| butyl methacrylate | 342.0 |
| butyl acrylate | 342.0 |
| styrene | 180.0 |
| methyl styrene dimer | 36.0 |
| DOWANOL PM | 48.0 |
| EXXATE 600 | 50.0 |
| Charge 4 | |
| di-t-amyl peroxide | 18.0 |
| DOWANOL PM | 18.0 |
| EXXATE 600 | 18.0 |
| Charge 5 | |
| di-t-amyl peroxide | 18.0 |
| DOWANOL PM | 18.0 |
| EXXATE 600 | 18.0 |

[1]Propylene glycol methyl ether, available from Dow Chemical Co.
[2]Hexyl acetate ester available from Exxon Chemicals America.
[3]t-amyl peroxyacetate, 60% in odorless mineral spirits, available from Atochem North America, Inc.

Charge 1 was added to a suitable reactor equipped with a condenser and mechanical agitation and heated to reflux (135° C.) under a nitrogen blanket. Charges 2 and 3 were each separately mixed. Charge 2 was added to the reactor over 3.5 hours. Addition of Charge 3 began 15 minutes after the beginning of Charge 2 and was carried out over a period of 3 hours. After the completion of Charges 2 and 3, the reaction was held at reflux for 1 hour. Charge 4 was then added over 30 minutes and the reaction held after the completion of this charge for 30 minutes. In a like manner, Charge 5 was added over 30 minutes and the reaction held for additional 2 hours. The resulting resin was a transparent material that had a final measured solids content of 61.7%, a viscosity of Y+ on the Gardner-Holdt scale, a number average molecular weight of 1529, and a weight average molecular weight of 3948 as determined by gel permeation chromatography.

EXAMPLE D

An amide acrylate monomer was prepared by transesterification from the following ingredients:

| Ingredients | Weight in grams |
| --- | --- |
| ethyl acrylate | 400.0 |
| 6-hydroxycaproamide of Example A | 131.0 |
| 4-methoxyphenol | 0.2 |
| triphenyl phosphite | 1.1 |
| dibutyltin oxide | 1.3 |

The first four ingredients were charged to a suitable flask equipped with an agitator, a Dean-Stark trap primed with ethyl acrylate, a condenser and an air sparge. The contents of the flask were heated to reflux (99° C.) and a small amount of $H_2O$ (approximately 1 g) was collected in the Dean-Stark trap. When $H_2O$ evolution ceased, the reaction was cooled to slightly below reflux temperature and the Dean-Stark trap was replaced with a Vigreux column and a partial take off condenser/distillation head. Dibutyltin oxide was then added to the reactor and the reaction mixture reheated to reflux. The reaction was held until the head temperature dropped to 81° C. (approximately 1 hour), at which time distillation of ethanol/ethyl acrylate azeotrope was begun. Removal of ethanol/ethyl acrylate continued until gas chromatographic analysis indicated nearly quantitative conversion of 6-hydroxycaproamide. Toward the end of the reaction, the pot temperature gradually increased to 110° C. and the head temperature to 92° C. The reaction flask was then equipped for simple vacuum distillation and excess ethyl acrylate stripped from the reaction at 80° C. under slightly reduced pressure. The air sparge was continued during the strip. The resulting product was a yellow oil that solidified almost immediately upon cooling. $^{13}C$ NMR and gas chromatographic analysis of the product indicated that it was greater than (>) 90% of the desired acrylate monomer.

EXAMPLE E

An acrylic copolymer of the amide acrylate monomer of the previous example was prepared from the following ingredients:

| Ingredients | Weight in grams |
| --- | --- |
| Charge 1 | |
| EKTAPRO EEP[1] | 58.3 |
| PROPASOL P[2] | 54.2 |
| Charge 2 | |
| LUPERSOL 555M60 | 25.0 |
| EKTAPRO EEP | 41.7 |
| Charge 3 | |
| 6-carboaminohexyl acrylate of Example D | 115.0 |
| methyl methacrylate | 1.5 |
| butyl methacrylate | 40.8 |
| butyl acrylate | 42.0 |
| styrene | 43.3 |
| acrylic acid | 5.0 |
| methyl styrene dimer | 2.5 |
| Charge 4 | |
| LUPERSOL 555M60 | 1.7 |
| EKTAPRO EEP | 1.7 |
| Charge 5 | |
| LUPERSOL 555M60 | 1.7 |
| EKTAPRO EEP | 1.7 |

[1]Ethyl-3-ethoxypropionate, avaiiable from Eastman Chemicals.
[2]Propylene glycol monopropyl ether, available from Union Carbide Corp.

Charge 1 was added to a suitable reactor equipped with a condenser and heated to reflux (150° C.) under a nitrogen blanket. Charges 2 and 3 were each separately mixed. Charge 2 was added to the reactor over 3 hours and 20 minutes. Addition of Charge 3 began 10 minutes after the beginning of Charge 2 and was carried out over a period of 3 hours. After the completion of Charges 2 and 3, the reaction was held at reflux for 1 hour. Charge 4 was then added and the reaction held after the completion of this charge for 1 hour. In a like manner, Charge 5 was added and the reaction held for additional 1.5 hours. The resulting resin was a transparent material that had a final measured solids content of 60.7%, a viscosity of V on the Gardner-Holdt scale, a number average molecular weight of 1845, and a weight average molecular weight of 3608 as determined by gel permeation chromatography.

EXAMPLE F

A material with both hydroxyl and N-methyl amide functional groups was prepared from the following ingredients:

| Ingredients | Weight in grams |
| --- | --- |
| methylamine (40% in $H_2O$) | 803.0 |
| ε-caprolactone | 803.0 |

Methylamine (40% in $H_2O$) was charged to a suitable reactor and cooled to 5° C. with an ice bath. ε-caprolactone was added to the reactor over 1.25 hours at a rate such that the reaction temperature did not exceed 5° C. Gas chromatographic analysis of the reaction mixture the following day showed that the reaction had proceeded to completion as determined by consumption of ε-caprolactone. The reaction was allowed to warm to room temperature. The reactor was equipped for vacuum distillation and $H_2O$ was stripped from the reaction at a vacuum of 1 mm Hg and a maximum temperature of 50° C. The resulting product was a yellow liquid which $^1H$ NMR analysis confirmed was the desired product N-methyl 6-hydroxycaproamide.

EXAMPLE G

An N-methyl amide methacrylate monomer was prepared from the following ingredients:

| Ingredients | Weight in grams |
| --- | --- |
| N-methyl 6-hydroxycaproamide of Example F | 239.3 |
| methacrylic anhydride | 304.9 |
| 4-dimethylaminopyridine | 0.5 |
| triphenyl phosphite | 0.5 |
| 2,6-di-t-butyl-4-methylphenol | 0.5 |
| toluene | 544.5 |
| sodium hydroxide | 99.0 |
| deionized H$_2$O | 544.5 |
| deionized H$_2$O | 247.5 |
| deionized H$_2$O | 247.5 |
| deionized H$_2$O | 247.5 |

The first five ingredients were charged to a suitable reactor and heated to 80° C. The reaction was held at this temperature until most (>95%) of the N-methyl 6-hydroxycaproamide was consumed. The reaction was allowed to cool and toluene was added to the reaction mixture, followed by the sodium hydroxide/deionized H$_2$O solution. The reactor contents were allowed to stir for 15 minutes, then were transferred to a separatory funnel. The organic and aqueous phases were separated. The organic phase was washed with three equivalent portions of deionized H$_2$O. The organic phase was then subjected to gas chromatographic analysis; since the level of remaining methacrylic anhydride and methacrylic acid by product was deemed unacceptable, the extraction sequence was repeated. The organic phase was then returned to the reactor and toluene stripped under reduced pressure to yield a light yellow liquid that was found by gas chromatographic analysis to be approximately 90% pure.

EXAMPLE H

An acrylic copolymer with the N-methyl amide methacrylate monomer of the previous example was prepared from the following ingredients:

| Ingredients | Weight in grams |
| --- | --- |
| Charge 1 | |
| EKTAPRO EEP | 70.0 |
| PROPASOL P | 65.0 |
| Charge 2 | |
| LUPERSOL 555M60 | 25.0 |
| EKTAPRO EEP | 50.0 |
| Charge 3 | |
| N-methyl 6-carboaminohexyl methacrylate monomer of Example G | 169.0 |
| methyl methacrylate | 1.5 |
| butyl methacrylate | 41.7 |
| butyl acrylate | 42.9 |
| styrene | 44.4 |
| acrylic acid | 6.0 |
| methyl styrene dimer | 3.0 |
| Charge 4 | |
| LUPERSOL 555M60 | 2.0 |
| EKTAPRO EEP | 2.0 |

-continued

| Ingredients | Weight in grams |
| --- | --- |
| Charge 5 | |
| LUPERSOL 555M60 | 2.0 |
| EKTAPRO EEP | 2.0 |

Charge 1 was added to a suitable reactor equipped with a condenser and heated to reflux (154.5° C.) under a nitrogen blanket. Charges 2 and 3 were each separately mixed. Charge 2 was added to the reactor over 3 hours and 20 minutes. Addition of Charge 3 began 10 minutes after the beginning of Charge 2 and was carried out over a period of 3 hours. After the completion of Charge 3, the reaction was held at reflux for 1 hour. Charge 4 was then added and the reaction held after the completion of this charge for 1 hour. In a like manner Charge 5 was added and the reaction held for additional 1.5 hours. The resulting resin was a transparent material that had a final measured solids content of 65.0%, a viscosity of W- on the Gardner-Holdt scale, a number average molecular weight of 1451, and a weight average molecular weight of 3478 as determined by gel permeation chromatography.

EXAMPLE I

A material with both amide and acrylate functionality was prepared from the following ingredients:

| Ingredients | Weight in grams |
| --- | --- |
| isophorone diisocyanate | 600.8 |
| EXXATE 600 | 555.0 |
| dibutyltin dilaurate | 4.7 |
| 6-hydroxycaproamide of Example E | 428.8 |
| dibutyltin dilaurate | 4.7 |
| 2,6-di-t-butyl-4-methylphenol | 2.3 |
| hydroxyethyl methacrylate | 281.0 |
| n-propanol | 262.0 |

Isophorone diisocyanate, EXXATE 600, and dibutyltin dilaurate were charged to a suitable reactor and heated to 60° C. 6-hydroxycaproamide was added to the reaction over a period of 2 hours 10 minutes such that the reaction temperature was maintained below 65° C. The reaction was then held until the isocyanate equivalent weight was essentially constant. Dibutyltin dilaurate and 2,6-di-t-butyl-4-methylphenol were then added to the reactor. The reaction temperature was then raised to 68° C. and hydroxyethyl methacrylate was added to the reactor over 1 hour 50 minutes. The reaction was held until no isocyanate could be detected by infrared spectroscopy and thinned with n-propanol to a theoretical solids excluding catalysts and inhibitors of 61.3%.

EXAMPLE J

An acrylic polymer with pendent amide and hydroxyl groups was prepared from the following ingredients:

| Ingredients | Weight in grams |
| --- | --- |
| Charge 1 | |
| n-propanol | 24.0 |
| EXXATE 600 | 141.0 |

-continued

| Ingredients | Weight in grams |
|---|---|
| Charge 2 | |
| LUPERSOL 555M60 | 49.0 |
| EXXATE 600 | 35.4 |
| Charge 3 | |
| material of Example I | 599.5 |
| hydroxypropyl acrylate | 147.0 |
| styrene | 66.2 |
| butyl acrylate | 66.2 |
| butyl methacrylate | 66.2 |
| acrylic acid | 14.7 |
| methyl styrene dimer | 7.4 |
| EXXATE 600 | 35.4 |
| Charge 4 | |
| LUPERSOL 555M60 | 12.3 |
| EXXATE 600 | 6.5 |

Charge 1 was added to a suitable reactor equipped with a condenser and agitator and heated to reflux (141° C.) under a nitrogen blanket. Charges 2 and 3 were each separately mixed. Charge 2 was added to the reactor over 3.5 hours. Addition of Charge 3 began 15 minutes after the beginning of Charge 2 and was carried out over a period of 3 hours. After the completion of Charge 3, the reaction was held at reflux for 1 hour. Charge 4 was then added over 0.5 hour and the reaction held after the completion of this charge for an additional 1 hour. The resulting resin had theoretical solids of 60.8%, a viscosity of >Z6 on the Gardner-Holdt scale, a number average molecular weight of 4984, and a weight average molecular weight of 10,077 as determined by gel permeation chromatography using a polystyrene standard.

EXAMPLE K

An amide methacrylate monomer was prepared from the following ingredients:

| Ingredients | Weight in grams |
|---|---|
| mixture of methyl 6-hydroxy-caproate/6-hydroxycaproamide[1] | 131.00 |
| methacrylic anhydride | 184.8 |
| 4-dimethylaminopyridine | 0.32 |
| 2,6-di-t-butyl-4-methylphenol | 0.32 |
| triphenyl phosphite | 0.32 |
| toluene | 334.0 |
| sodium hydroxide | 61.6 |
| deionized $H_2O$ | 334.0 |

[1]Prepared by heating e-caprolactone and ammonia in methanol solution under pressure at 50° C.

To a flask equipped with a mechanical stirrer, thermocouple, and condenser were added methyl 6-hydroxycaproate/6-hydroxycaproamide mixture, methacrylic anhydride, 2,6-di-t-butyl-4-methylphenol, and triphenyl phosphite. The contents were heated to 100° C. and held until ~98% of methyl 6-hydroxycaproate/6-hydroxycaproamide was consumed as indicated by gas chromatography. The contents were cooled to room temperature and toluene was added. The product was a pale yellow oily liquid.

EXAMPLE L

A material with hydroxyl and N-methyl amide functional groups was prepared from the following ingredients:

| Ingredients | Weight in grams |
|---|---|
| methylamine (40% in $H_2O$) | 1192.0 |
| ethyl lactate | 1396.0 |

The first ingredient was charged to a flask equipped with a agitator under an nitrogen blanket. Ethyl lactate was added to the flask over 1 hour and 9 minutes at a rate such that the reactor temperature did not exceed 30° C. An ice bath was also placed under the flask during the addition to control the reaction temperature. After standing at room temperature overnight, analysis of the reaction mixture by gas chromatography indicated quantitative consumption of ethyl lactate. The flask was then equipped for vacuum distillation, the reaction mixture heated to 60° C., and $H_2O$ and by-product ethanol were stripped from the reaction under reduced pressure. When no more distillate was coming off the reaction, the flask was equipped with a Dean-Stark trap and toluene (500 g) was added to the reaction product. The reaction was held at 55° C. and sufficient vacuum was applied to the system to attain reflux. After 1 hour, the flask was reequipped for vacuum distillation and the toluene removed under reduced pressure. Residual $H_2O$ was observed in the toluene distillate. Additional toluene (100 g) were added to the system and likewise stripped from the reaction. The resulting material was a yellow oil with an acid value of 55.5. $C^{13}$NMR and gas chromatographic analysis indicated that the material was approximately 95% of the desired product, the major impurity being lactic acid formed by hydrolysis of ethyl lactate.

EXAMPLE M

An N-methyl substituted amide functional acrylic monomer, 1-(N-methylcarboamino)-ethyl methacrylate, was prepared as follows:

To a flask equipped with a condenser, thermocouple, and mechanical stirrer were charged N-methyl lactamide of EXAMPLE L (204.0 g, 2.0 moles), methacrylic anhydride (360.0 g, 2.2 moles, 94%), 2,6-di-t-butyl-4-methylphenol (1.1 g), triphenylphosphite (0.55 g), and N,N-dimethylaminopyridine (0.55 g). The contents were stirred at 100° C. until all of the N-methyllactamide was consumed as indicated by gas chromatography. Upon cooling to room temperature, toluene (400.0 g) was added followed by a solution of sodium hydroxide (104.0 g) in deionized water (400.0 g). The suspension was stirred for 1 hour and the contents were transferred to a separatory funnel. The aqueous layer was removed and the organic layer was twice rinsed with deionized water. The remaining organic phase was vacuum stripped of toluene at 60° C., leaving the methacrylate product as a yellow oil. Purity as indicated by gas chromatography was 90–95%.

EXAMPLE N

An N-methyl substituted amide functional acrylic copolymer containing 1-(N-methylcarboamino)-ethyl methacrylate was prepared as follows:

A flask equipped with a mechanical stirrer, thermocouple, condenser, and nitrogen inlet was charged with EKTAPRO EEP (70 g) and PROPASOL P (65 g). The contents were heated to reflux (150° C.), and the initiator and monomer feeds were simultaneously added over 3 hours. The reaction mixture was then held at 140° C. for 1 hour at which time the two chase feeds were added at 1 hour intervals. The reaction temperature was maintained at 140° C. for 1.5 additional hours to yield the acrylic resin.

| Initiator Feed | |
|---|---|
| LUPERSOL 555 | 25.0 g |
| EKTAPRO EEP | 50.0 g |
| Monomer Feed | |
| 1-(N-methylcarboamino)-ethyl methacrylate of EXAMPLE M | 129.0 g |
| Butyl Acrylate | 42.0 g |
| Butyl Methacrylate | 63.0 g |
| Styrene | 55.5 g |
| Acrylic Acid | 6.0 g |
| Methyl Methacrylate | 1.5 g |
| α-Methylstyrene Dimer | 3.0 g |
| Chase Feed 1 | |
| LUPERSOL 555 | 2.0 g |
| EKTAPRO EEP | 2.0 g |
| Chase Feed 2 | |
| LUPERSOL 555 | 2.0 g |
| EKTAPRO EEP | 2.0 g |

The resulting acrylic resin had a solids content of 60.7% (110° C./1 hr.), and Z+ viscosity (Gardner-Holdt).

We claim:

1. An ethylenically unsaturated compound having the structure:

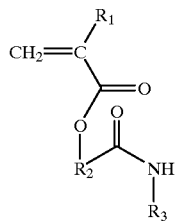

wherein $R_1$ is hydrogen or methyl, $R_2$ is an alkylene group having 2 to 20 carbon atoms, and $R_3$ is hydrogen or lower alkyl having 1 to 4 carbon atoms; wherein when $R_3$ is hydrogen and $R_2$ has two carbon atoms, $R_2$ is methyl methylene.

2. The compound of claim 1 wherein $R_2$ is selected from the group consisting of methyl methylene, ethylene, methyl ethylene, propylene, dimethyl propylene, butylene, and pentylene.

3. The compound of claim 1 wherein $R_3$ is lower alkyl having 1 to 4 carbon atoms.

4. The compound of claim 1 wherein $R_3$ is selected from the group consisting of hydrogen, methyl, and butyl.

5. The compound of claim 4 wherein $R_3$ is methyl or butyl.

6. The compound of claim 1 wherein said compound is derived from a hydroxyl functional amide reacted with methacrylic anhydride via esterification.

7. The compound of claim 6 wherein said hydroxyl functional amide is derived from a lactone ring-opened with ammonia or a primary amine.

8. The compound of claim 7 wherein said lactone is epsilon-caprolactone.

9. The compound of claim 7 wherein said lactone is ring-opened with a primary amine selected from the group consisting of methylamine, ethylamine and propylamine.

10. The compound of claim 6 wherein said hydroxyl functional amide has the following structure:

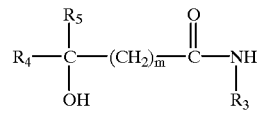

where $R_3$, $R_4$ and $R_5$ are each independently hydrogen or lower alkyl having 1 to 4 carbon atoms and m is an integer from 0 to 3.

11. The compound of claim 1 wherein said compound is derived from an acrylic acid ester or methacrylic acid ester transesterified with a hydroxyl functional amide.

12. An amide monomer having the structure:

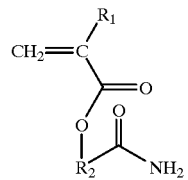

wherein $R_1$ is hydrogen or methyl, and $R_2$ is an alkylene group having 2 to 20 carbon atoms, wherein when $R_2$ has two carbon atoms, it is methyl methylene.

* * * * *